United States Patent
Xu et al.

(10) Patent No.: US 11,879,866 B2
(45) Date of Patent: Jan. 23, 2024

(54) MEASURING CONCENTRATIONS OF MIXED GASES AT AN ENDPOINT

(71) Applicant: ROMET LIMITED, Mississauga (CA)

(72) Inventors: Chang Qing Xu, Dundas (CA); Liam Flannigan, Hamilton (CA); Joshua Kneller, Hamilton (CA); Frederick Joseph Maly, Jr., Oakville, MO (US)

(73) Assignee: ROMET LIMITED, Mississauga (CA)

( * ) Notice: Subject to any disclaimer, the term of this patent is extended or adjusted under 35 U.S.C. 154(b) by 12 days.

(21) Appl. No.: 17/560,082

(22) Filed: Dec. 22, 2021

(65) Prior Publication Data

US 2022/0196602 A1     Jun. 23, 2022

Related U.S. Application Data

(60) Provisional application No. 63/129,863, filed on Dec. 23, 2020.

(51) Int. Cl.
| | |
|---|---|
| *G01N 29/02* | (2006.01) |
| *G01N 29/024* | (2006.01) |
| *G01N 33/00* | (2006.01) |
| *G01K 13/00* | (2021.01) |
| *G08B 21/18* | (2006.01) |

(52) U.S. Cl.
CPC ........... *G01N 29/024* (2013.01); *G01K 13/00* (2013.01); *G01N 33/0027* (2013.01); *G08B 21/182* (2013.01); *G01N 2291/011* (2013.01); *G01N 2291/0212* (2013.01); *G01N 2291/102* (2013.01)

(58) Field of Classification Search
CPC ............. G01N 29/024; G01N 33/0027; G01N 2291/011; G01N 2291/0212; G01N 2291/102; G01N 2291/02809; G01N 29/222; G01K 13/00; G08B 21/182
See application file for complete search history.

(56) References Cited

U.S. PATENT DOCUMENTS

| | | | |
|---|---|---|---|
| 3,788,141 A * | 1/1974 | Blackwell | ............. G01F 1/3282 73/861.23 |
| 4,345,463 A * | 8/1982 | Wilson | ............... G01N 30/8658 73/23.35 |
| 4,662,212 A | 5/1987 | Noguchi et al. | |
| 5,625,140 A * | 4/1997 | Cadet | ................... G01N 29/222 73/24.01 |

(Continued)

FOREIGN PATENT DOCUMENTS

| | | |
|---|---|---|
| GB | 2215049 A | 9/1989 |
| WO | 1999015870 A1 | 4/1999 |

OTHER PUBLICATIONS

International Search Report dated Mar. 7, 2022 For Corresponding International PCT Patent Application No. PCT/CA2021/051880; 4 Pages.

(Continued)

*Primary Examiner* — Tarun Sinha

(57) ABSTRACT

In accordance with embodiments there is proposed an ultrasound sensor device and an ultrasound sensor system configured to perform a method using ultrasound to determine a ratio or concentration of respective gases in a flow of mixed gases. There is provided a method to adapt a distribution system with an ultrasound sensor device and/or an ultrasound sensor system.

20 Claims, 4 Drawing Sheets

(56) References Cited

U.S. PATENT DOCUMENTS

| | | | | |
|---|---|---|---|---|
| 7,823,463 | B1* | 11/2010 | Feller | G01F 1/667 |
| | | | | 73/861.27 |
| 8,666,683 | B2* | 3/2014 | Rogers | G01M 3/2892 |
| | | | | 702/45 |
| 2002/0062681 | A1* | 5/2002 | Livingston | G01N 29/348 |
| | | | | 73/24.01 |
| 2004/0093948 | A1* | 5/2004 | Kelner | G01N 29/449 |
| | | | | 73/597 |
| 2017/0315098 | A1* | 11/2017 | Beers | G01N 29/42 |

OTHER PUBLICATIONS

Written Opinion dated Mar. 7, 2022 For Corresponding International PCT Patent Application No. PCT/CA2021/051880; 4 Pages.

* cited by examiner

MEASURING CONCENTRATIONS OF MIXED GASES AT AN ENDPOINT

CROSS-REFERENCE

This application claims a domestic benefit from U.S. Provisional Application No. 63/129,863, filed Dec. 23, 2020, the entire contents of which are incorporated herein by reference.

FIELD

This disclosure relates to gas metering and gas meter sets and more particularly to measuring concentrations of mixed gases at an endpoint of a distribution system.

BACKGROUND

Current gas measuring apparatuses measure the volume of a particular gas being measured. When two or more gases are mixed together the measuring apparatus measures the volume of both gases as if they are one gas. With the introduction of mixing gases, for example hydrogen, landfill gas, natural gas, etcetera, the measuring apparatus requires a means to determine the concentration of each gas in the mix.

SUMMARY

In accordance with embodiments there is proposed an ultrasound sensor device and an ultrasound sensor system configured to perform a method using ultrasound to determine a ratio or concentration of respective gases in a flow of mixed gases. There is provided a method to adapt a distribution system with an ultrasound sensor device and/or an ultrasound sensor system.

In an first aspect there is an ultrasound sensor device comprising: a measuring chamber; and an ultrasound sensor coupled to the measuring chamber to generate ultrasound signals with which to determine a speed of sound in a flow of mixed gas in the measuring chamber. The ultrasound sensor is coupled to provide ultrasound signals or the speed of sound to a processing unit, the processing unit is configured to determine a concentration of the respective gases in the mixed gas in response to the speed of sound; and the processing unit is further configured to present at least one of the speed of sound, the concentration of the respective gases and other data determined from the speed of sound.

The ultrasound sensor device of the first aspect can comprise a temperature sensor to measure temperature in the chamber, the temperature sensor providing temperature signals to the processing unit with which to determine data determined from the speed of sound.

In the ultrasound sensor device of the first aspect, the ultrasound sensor can comprises a sensor wave generator and sensor wave detector, preferably positioned on a same side of the measuring chamber to receive a reflected wave signal.

In the ultrasound sensor device of the first aspect, the measuring chamber can be a pre-existing component of a distribution system adapted with the ultrasound sensor.

In a second aspect, there is provided an ultrasound sensor system comprising the ultrasound sensor device of any of the preceding claims and a controller board comprising a processing unit coupled thereto.

In any aspect, the processing unit can be configured to determine the concentration of the respective gases in accordance with the adiabatic constant of the mixed gas and the mole value of the mixed gas.

In any aspect, the processing unit can determine the concentration of the respective gases in accordance with the speed of sound in the mixed gas $V_s$ in accordance with the equation:

$$V_s = \sqrt{\frac{\gamma RT}{M}},$$

where $\gamma$ is the adiabatic constant of the mixed gas, R is the gas constant, T is the temperature and M is the molar mass of the mixed gas. If the mixed gas is a binary gas, $\gamma$ can be determined with the equation:

$$\gamma_{mixture} = 1 + \left(\frac{X}{\gamma_1 - 1} + \frac{1-X}{\gamma_2 - 1}\right)^{-1}$$

where X is the molar fraction of a first gas of the mixed gas; and
M can be determined with the equation:

$$M_{mixture} = XM_1 + (1-X)M_2$$

where $M_1$ and $M_2$ are the molar mass of the first gas and a second gas of the mixed gas.

In any aspect, the processing unit can be configured (e.g. a priori) to know a gas type of each gas in the mixed gas.

In any aspect, the processing unit can be coupled to an alarm device, the processing unit signalling an alarm in response to a measuring chamber threshold.

In any aspect, the processing unit can be coupled to a control system, the processing unit providing a control signal in response to a measuring chamber threshold to control a flow within the measuring chamber.

In any aspect, the processing unit can be coupled to an off-board device to communicate any one of the speed of sound and data determined from the speed of sound.

In a third aspect there is provided a meter set comprising a meter body and an ultrasound system of the second aspect, wherein the meter body comprises the measuring chamber, wherein a meter set processing unit comprises the processing unit of the ultrasound system and wherein the ultrasound sensor is positioned to measure the speed of sound in the meter set chamber.

In the third aspect, the meter set can comprise at least one of following coupled to the meter set processing unit: a pressure sensor to measure pressure in the meter set; and a flow sensor responsive to a flow of gas through the meter set to measure gas volume, flow rate or both.

In a fourth aspect there is provided a method to adapt a distribution system, the method comprising: selecting an existing component of the distribution system to define a measuring chamber; adapting the measuring chamber with an ultrasound sensor; determining a distance traveled of a wave signal generated and detected by the ultrasound sensor; and configuring a processing unit to determine and present at least one of a speed of sound of a mixed gas flowing in the measuring chamber and data determined from the speed of sound.

In the fourth aspect, the method can comprise adapting the measuring chamber with a temperature sensor coupled to the processing unit to provide temperature signals with which to determine determined from the speed of sound.

In the fourth aspect, the method can comprise configuring the processing unit with a measuring chamber threshold for use to provide at least one of an alarm signal and a control signal in response to operation of the distribution system outside the measuring chamber threshold.

DETAILED DESCRIPTION

Figure 1:
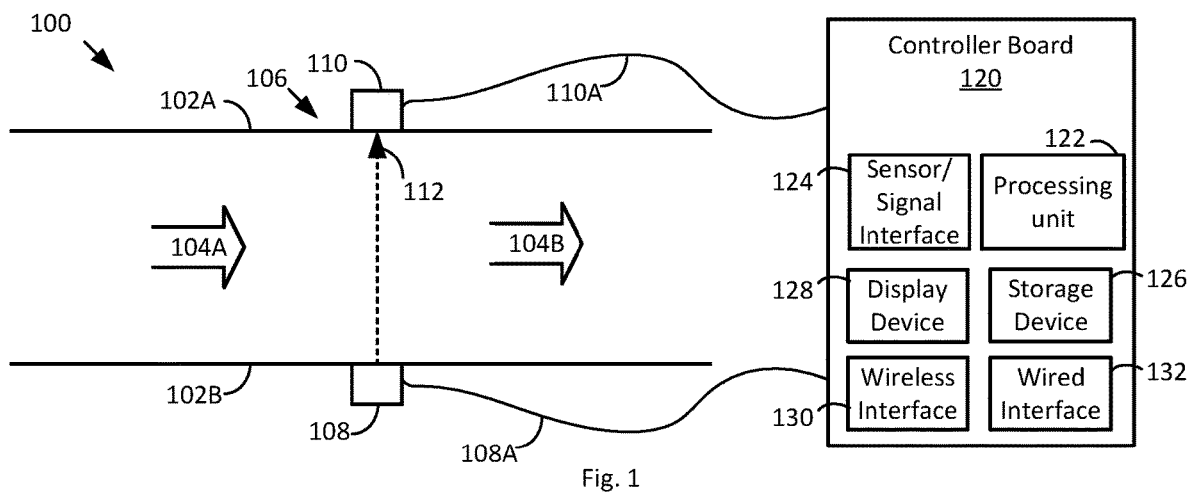
FIG. 1 is a block diagram of a portion of a distribution system configured to determine a concentration of mixed gases at an endpoint, in accordance with an embodiment.

Pipeline systems transport gases across continents. From the well, natural gas moves into the transmission system. Other gases, such as hydrogen, can be manufactured, landfill gas from landfills, and other gases can be introduced at various points throughout the transmission system. The transmission pipelines can be 100% of a particular gas or a mixture of multiple gases.

Many major intercontinental pipelines are "looped"—there are two or more lines running parallel to each other in the same right of way. This provides the opportunity for each pipeline to transport varying amounts of different mixed gases.

When the mixed gas in a transmission pipeline reaches a local gas utility, it normally passes through a "gate station", an endpoint of a transmission system. Utilities frequently have gate stations receiving gas at many different locations and from several different pipelines. At the gate station, the mixed gas can be separated either as a whole or part of the mix. By way of example, if a 50/50 mixed gas of hydrogen and natural gas is received, the whole of the 50% of natural gas could be removed or 30% of the hydrogen could be removed.

The mixed gas then passes through the gate station into the local distribution company's system. There can be one to dozens of transmission system endpoints depending on the size of the local distribution company. From there the mix gas travels through a series of various pipe sizes and pressures before arriving at the local distribution company endpoint or the customer's location for consumption. Depending on the size of the distribution system, the number of endpoints can range from thousands to millions. The local distribution company endpoints include residential, commercial, and industrial customers.

Gases are measured in volume and sold in units of energy. The conversion takes place in a computer billing system. The volume of the mix is measured at the endpoint of the transmission and/or the distribution system. Once the energy value is determined at several locations, this value is applied to all endpoints in the computer billing system.

By way of non-limiting example, a gas distribution company receives transmission gas at five locations (each a transmission endpoint) to distribute to 700,000 customers (each a distribution endpoint). At the five transmission endpoints only one is delivering mixed gas or 100% hydrogen gas that mixes with natural gas received at the other transmission endpoints. At that transmission endpoint the percentage of hydrogen, mixed in with the natural gas, is determine and applied to all 700,000 distribution endpoints/customers. Distribution endpoints/customers on the opposite side of the distribution system from the initial mix point will receive little, if any, of the mixed gas while distribution endpoints/customer closer to the mix point with receive all of the mixed gas.

This method does not accurately determine the amount of energy from mixed gases at each distribution endpoint. As the mixed gas passes through the transmission and distribution systems the concentration can, and does, change at each endpoint. Therefore some endpoints have a higher energy value and some endpoints have a lower energy value. To obtain a more accurate method of measuring mixed gas energy, the concentration of the mix is determined at each distribution system endpoint.

In an embodiment, a method, as further described, is provided to determine the concentration of mixed gases at each distribution endpoint and therefore the energy value at the distribution endpoint.

Mixed Gas with Unknown Ratio of Gas Components

If the mixed gas has an unknown ratio of gas components or one wants to make a more accurate measurement of the calorific value, then the ratio of gas components is measured. In accordance with the techniques and embodiments herein, there is provided an ultrasonic method to measure the ratio of gas components.

In an embodiment, the ultrasonic method involves sending an ultrasonic wave through the pipe or other chamber or container containing the gas. If the ultrasonic wave is transmitted perpendicular to the direction of gas flow, then the speed of the gas flow should not influence the speed of the ultrasonic wave. By measuring the time it takes the ultrasonic wave to travel the diameter of the pipe, one can calculate the speed of sound of the gas mixture.

FIG. 1 shows an illustration of a portion of a distribution system 100 at an endpoint thereof, in accordance with an embodiment. A container 102 (for example a measuring chamber), contains a flow of mixed gas, for example, a mix of two gases, that flow through the container as depicted by the arrows 104A and 104B.

The flow of mixed gas flows through a measuring point 106. At measuring point 106 there is positioned on opposite sides 102A and 102B of container 102 and perpendicular to flows 104A, 104B, a sensor wave generator 108 and a sensor wave detector 110. An ultrasonic wave 112 is depicted travelling between sensor wave generator 108 and sensor wave detector 110. Arrow 104A depicts a flow of gas prior to measurement (e.g. an unknown concentration of mixed gas), while arrow 104B depicts a flow of gas post-measurement (e.g. a known concentration of mixed gas).

Sensor wave generator 108 and sensor wave detector 110 are coupled to a micro-processor controller board 120 (e.g. having a processing unit 122) via a sensor/signal interface 124. In an embodiment the Sensor wave generator 108 and sensor wave detector 110 are coupled using respective lead lines 108A and 110A. The processing unit sends a signal to actuate the sensor wave generator and receives sensor wave detector data from wave detector 110. In an embodiment, the processing unit calculates a speed of sound in the mixed gas, for example, using ultrasound signals (data) from the sensors (e.g. 110) and a distance travelled between generator 108 and detector 110 over time determined by the processing unit. A storage device 126, coupled to the processing unit, stores data (e.g. the distance) and instructions for the processing unit, for example to configured its operations.

In an embodiment, the processing unit receives a speed of sound from the ultrasound sensors, such sensors calculating the speed using the distance travelled.

In an embodiment, the controller board outputs any one or more of the speed of sound in the mixed gas, and data calculated therefrom. Data calculated therefrom comprises any of a gas concentration or ratio of the mixed gas, respective moles of the respective gases and/or total moles in a volume of mixed gas, respective BTUs (or other energy equivalent) of the respective gases and/or total BTUs in a volume of mixed gas, etc.

In an embodiment, the controller board is coupled to one or more other sensors and is configured to determine other data such as, temperature, pressure, vibration, a flow rate of the mixed gas, a total volume of the mixed gas, and/or use other data such as to trigger a warning alarm signal, a control signal, etc.

In an embodiment, the container is a measuring chamber of a gas meter set configured to measure a flow of gas.

The processing unit may comprise a CPU, micro-controller, field programmable gate array (FPGA) or other type of integrated circuit configurable to perform as described.

In an embodiment, the processing unit is coupled to any one or more of: storage device 126 storing data and instructions to configure operations of the processing unit 122; a display device 128; a wireless communication interface 130 (e.g. comprising an antenna) for wireless communications; a wired communication interface 132 (e.g. comprising a port to couple cabling) for wired communications; an alarm device (not shown) (e.g. via sensor/signal interface 124) to signal an alarm condition; and a control system (not shown) (e.g. via sensor/signal interface 124) to control an operation of the fluid distribution system (e.g. to an actuated control valve, etc.).

In an embodiment, the alarm device is local and fixed in location to the measuring chamber. The alarm device comprises any of a light, a horn, a buzzer, a bell, etc.

In an embodiment, the control system is a local control to a component of the distribution to which the measuring chamber is coupled. The control system regulates a flow of fluid through at least a portion of the distribution system associated to the measuring chamber. Controlling the flow in the portion of the distribution system varies the flow through the measuring chamber and varies the vibrations (frequency) therein among other things. The control signal from the processing unit may be communicated to an intermediate control system (not shown) that uses logic etc. and which communicates with an actuator (e.g. to open or close or otherwise adjust a position and impact the flow) or the signal from the processing unit 122 may be (more) directly communicated to an actuator (e.g. without option for override).

In an embodiment (not shown), other input and/or output devices are coupled to the processing unit 122 (e.g. buttons, keys, lights, bell, other sensors, etc.).

In an embodiment sensor/signal interface 124 comprises applicable types to receive and/or transmit signals such as data signals from sensors or control signals to the sensor wave generator, an alarm and/or a control system.

In an embodiment, the sensor wave generator has a local controller and is not controlled via the controller board 120.

It will be understood that the sensor/signal interface 124 may be provided by one or both of the wireless and wired interfaces 130 and 132 depending on how the sensors, alarm device and control system are configured, etc.

In an embodiment, the processing unit 122 presents (e.g. provides for display, communicates, etc.) at least one of the speed of sound in the gas and data determined from the speed. In an embodiment, the data is communicated such as via a message to an off-board device (not shown) via the wireless communication interface 120 using short range or long-range wireless communication; or via the wired communication interface 122 for wired communication.

In an embodiment, an off-board device comprises a computing device for monitoring the endpoint and may comprise or communicate with a billing system associated to the distribution system. In an embodiment, the off-board device comprises a smartphone, tablet or other personal computing device of a user responsible to monitor at least a portion of a distribution system to which the measuring chamber is coupled. Such communication may be made via a centralized monitoring and/or control system (itself an off-board device) in communication with the personal computing device.

In an embodiment, the speed of sound in the gas and data determined from the speed is communicated via the display device 118. In an embodiment, the speed of sound in the gas and data determined from the speed is stored to storage device 116.

In an embodiment, the other data is communicated. The other data may be communicated in any of the manners as described in relation to the speed of sound and data determined from it.

In an embodiment, the processing unit 122 is configured to determine whether the pressure, frequency, flow rate and/or total volume, or other measure is outside an applicable measuring chamber threshold (e.g. exceeds a range of normal operation of the distribution system associated with the chamber). That is there may be one only or more than one measuring chamber threshold. In an embodiment, for example, only flow rate is so monitored. In another embodiment, pressure and vibration are so monitored, etc. The applicable measuring chamber threshold is stored in storage device 116. In an embodiment, in response, the processing unit 122 communicates one or both of an alarm signal to the alarm device and a control signal to the control system to bring the pressure, frequency, flow rate and/or total volume back or other measure to within the applicable measuring chamber threshold. In an embodiment, the processing unit 122 communicates an alarm message to an off-board device using wireless or wired communications. The alarm message to the off-board device may be in addition to communicating to the alarm device or in the alternative to such communicating to the alarm device.

In an embodiment, the processing unit 122 has multiple applicable measuring chamber thresholds where a first is associated to an alarm signal and a second is associated to a control signal to control operations. In an embodiment, the measuring chamber thresholds are associated to respective alarm severities.

The measuring chamber is associated with a known volume useful to the processing unit 122. The chamber may comprise a length of piping in the distribution system, a meter set body, or other apparatus integral to the distribution system. The measuring chamber may comprise a metal body or a non-metal body.

To increase the accuracy of a speed of sound measurement, in an embodiment, the ultrasonic wave generator and detector are placed on the same side of the container. In such a configuration the detector detects a reflected wave, which doubles the distance the wave travels. This in turn increases the time of flight of the wave and results in increased accuracy of the speed of sound. See FIGS. 2 and 3 for an illustration thereof.

Figure 2:
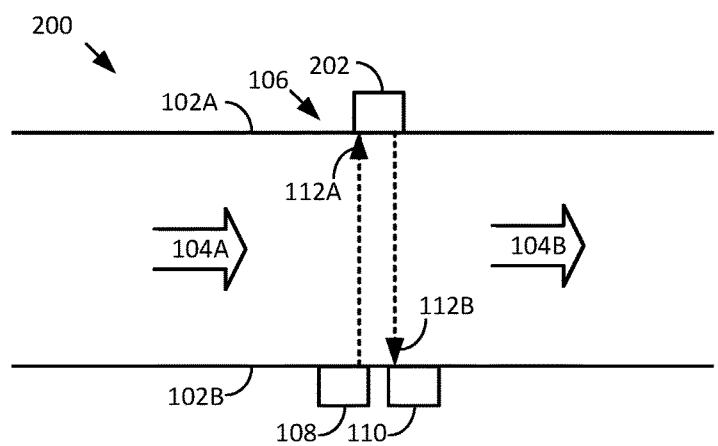
FIG. 2 is a block diagram of a portion of a distribution system configured to determine a concentration of mixed gases at an endpoint, in accordance with an embodiment.

FIG. 2 shows an illustration of a portion of a distribution system 200 at an endpoint thereof, in accordance with an embodiment. In the embodiment of FIG. 2, the sensor wave generator 108 and sensor wave detector 110 are on a same side (e.g. 102B) of container 102 and a reflective sensor 202 is positioned oppositely at side 102A of measuring point 106. The ultrasonic wave is depicted with two components 112A and 112B. Though not depicted it will be understood that sensor wave generator 108 and sensor wave detector 110 are coupled to a controller board 120 such as shown in FIG. 1. Embodiments thereof are applicable to portion of distribution system 200 but having a longer distance of travel (2×) for the wave signal.

Figure 3:
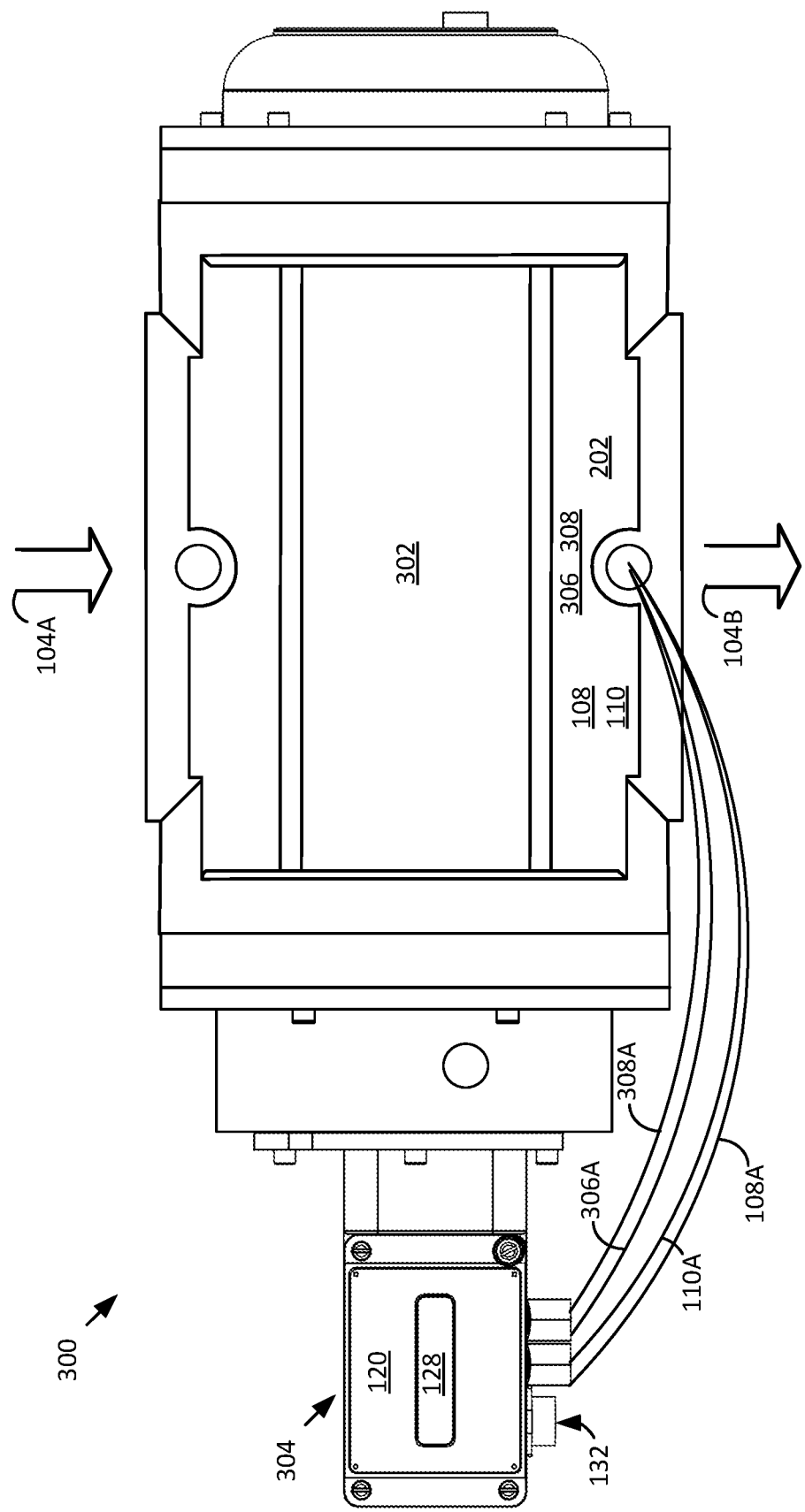
FIG. 3 is an illustration of a gas meter set configured to determine a concentration of mixed gases at an endpoint, in accordance with an embodiment.

FIG. 3 is an illustration of a gas meter set 300 configured to determine a concentration of mixed gases at an endpoint of a distribution system (e.g. when installed), in accordance with an embodiment. In the example shown, gas meter set 300 comprises a rotary gas meter body 302. Mounted thereon in a housing 304 is controller 120 having a processing unit 122. Respective lead lines 108A and 110A couple sensor wave generator 108 and sensor wave detector 110 mounted within the gas meter body 302 (e.g. on one side of a chamber (not shown) through which the gas flows). On an opposite side of the chamber is mounted therein a reflective sensor 202. Positioned within the meter body 302 such as in the chamber is a pressure sensor 306 having a lead 306A coupling to the processing unit to measure pressure therein. In another embodiment (not shown), the lead 306A is a tube open to the pressure of the chamber and a pressure sensor is located in housing 304. Positioned within the meter body 302 such as in the chamber is a temperature sensor 308 having a lead 308A coupling to the processing unit to measure temperature therein.

Other sensors or inputs may be coupled to the processing unit (not shown) such as for measuring a volume of gas flowing through the meter body 302. In a rotary meter, lobed bodies (not shown) within the meter body 302 are mounted for rotation by the flow of gas through the meter 300. A fixed volume is measured with each rotation. The rotation is measured and used to calculate a volume measure and a flow rate, etc. Processing unit 122 in the various embodiments determines the gas ratio according to the following principals. Since the speed of sound of a gas mixture is dependent on the ratio of the gas components in the mixture, knowing the speed of sound will allow for the ratio to be determined. The speed of sound of a gas, including a mixed gas, is given by the equation:

$$V_s = \sqrt{\frac{\gamma RT}{M}},$$

where γ is the adiabatic constant (also known as the adiabatic index or heat capacity ratio) of the (mixed) gas, R is the gas constant, T is the temperature and M is the molar mass of the (mixed) gas. Once the speed of sound of the mixed gas is known the following equations can be derived:

$$\gamma_{mixture} = \frac{MV_s^2}{RT}$$

$$M_{mixture} = \frac{\gamma RT}{V_s^2}$$

This equation can be solved to calculate X binary gas mixture:

$$\gamma_{mixture} = 1 + \left(\frac{X}{\gamma_1 - 1} + \frac{1-X}{\gamma_2 - 1}\right)^{-1}$$

where X is the molar fraction of the first gas. M is calculated with the equation:

$$M_{mixture} = XM_1 + (1-X)M_2$$

where M1 and M2 are the molar mass of the first and second gas components in the mixture.

In an embodiment, concentrations of gas can be mixed at known ratios and the speed of sound measured at each. The measurements are useful to define a table and/or a function that may map a measured speed of sound to a concentration of gases. The relationship is responsive to the above equations but the equations themselves need not be solved for each measure of the speed of sound.

Table 1 represents the velocity $V_s$ of a mixed gas. In this example X=0 corresponds to pure hydrogen while X=1 is pure methane (e.g. X=0 represents 0% methane and X=1 represents 100% methane). If the velocity equals 606.5, the percent of hydrogen is 50% and the percent of natural gas is 50%. Therefore the number of moles of each gas can be determined. It is understood that X may represent the percentage of hydrogen and the velocity numbers in Table 1 may be reordered accordingly.

TABLE 1

| X | Vs |
|---|---|
| 0 | 1305.7 |
| 0.1 | 999.27 |
| 0.2 | 838.46 |
| 0.3 | 735.39 |
| 0.4 | 662.08 |
| 0.5 | 606.5 |
| 0.6 | 562.48 |
| 0.7 | 526.6 |
| 0.8 | 496.38 |
| 0.9 | 470.68 |
| 1 | 448.43 |

Figure 4:
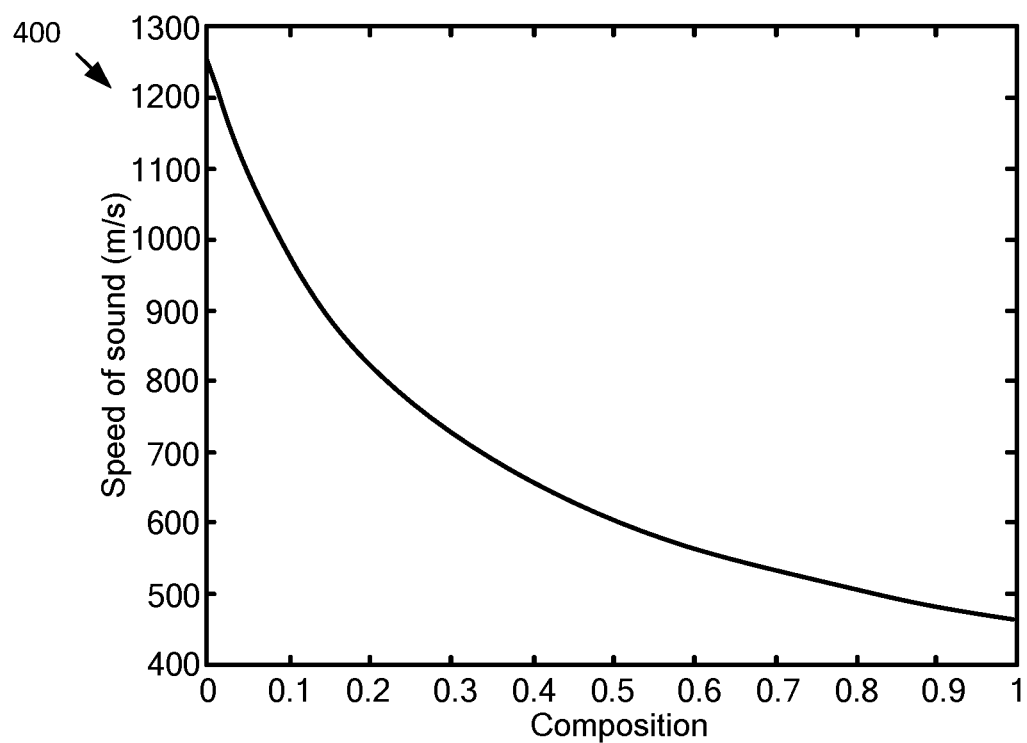
FIG. 4 is a graph showing a relationship between speed of sound and a mixed gas composition measure X on a scale of 0-1.

FIG. 4 is a graph 400 showing a plotted relationship (e.g. definable by a function) between the speed of sound Vs and a mixed gas composition measure X on a scale of 0-1 such as shown in Table 1.

Figure 5:
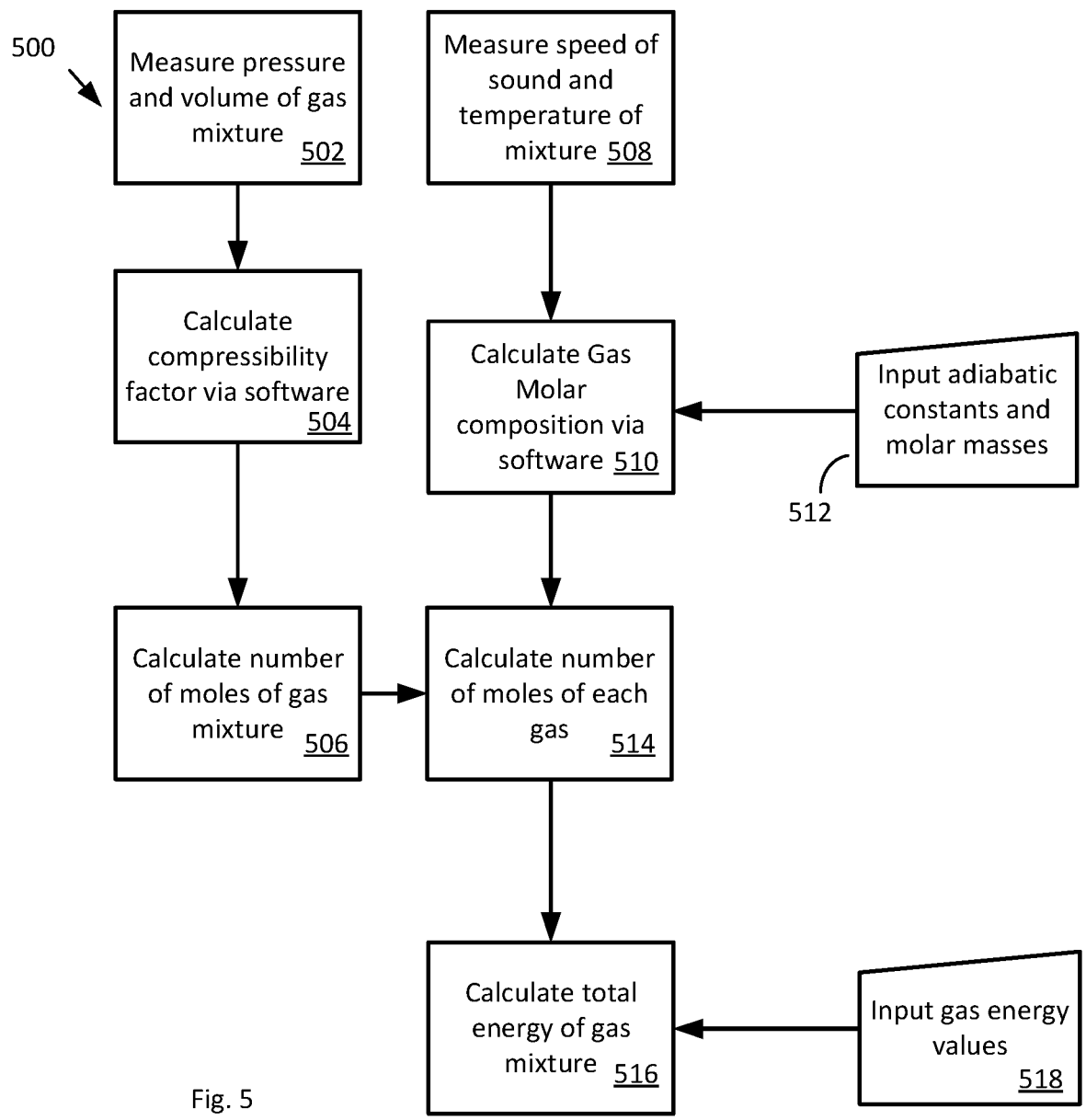
FIG. 5 is a flowchart of operations in accordance with an embodiment.

FIG. 5 is a flowchart of operations 500, such as operations of a processing unit 122, in accordance with an embodiment. At 502 operations measure pressure and volume of the mixed gas. At 504, a compressibility factor is measured (e.g. responsive to the ideal gas law). At 506, the number of mols of gas is calculated.

At 508, the speed of sound and temperature in the gas is measured. (It is understood that operations herein may be separated into sub operations). At 510, gas molar composition is determined. Inputs 512 are useful for such calculations such as the adiabatic constants and the molar masses. Inputs 512 may be stored in storage device 126.

At 514, the number of moles of each gas is determined using output of operations 510 and 506. At 516 total energy of the gas mixture is calculated. Gas energy values as inputs (518) are useful and may be stored in storage device 126.

In an embodiment (not shown), the operations 500 are performed partially by meter set 300 (having a processing unit 122) and partially by a remotely located computing unit (not shown) having a respective processing unit. The remotely located computing unit is in communication with the meter set 300. In an embodiment, meter set 300 performs operations 502 and 508 to measure gas data values (e.g. pressure, flow, temperature and speed of sound) and communicates such gas data to the remotely located computing unit to perform other calculations. Processing unit 122 may perform additional steps of operations 500 and send results accordingly, for example, any of steps 504, 506, 510, and 514.

EXAMPLE

By way of example for a mixed gas comprising methane and hydrogen, Table 2 provides values for the respective moles per cubic foot, Table 3 provides values for the respective BTUs per mole and Table 4 provides values for respective total moles, and BTUs of particular concentrations of the gases at a volume of 100 cubic feet:

TABLE 3

| Moles F$^3$ | |
|---|---|
| Methane | 0.978 |
| Hydrogen | 1.152 |

TABLE 3

| | |
|---|---|
| BTU per Mole Methane | 1007.3 |
| BTU per Mole Hydrogen | 374.4 |

TABLE 4

| | CF | Hydrogen | Methane | Total Moles Hydrogen | Total Moles Methane | Total BTU Hydrogen | Total BTU Methane | Mixed Gas BTU |
|---|---|---|---|---|---|---|---|---|
| 5% Mixed Hydrogen | 100 | 5.0% | 95.0% | 5.76 | 92.91 | 2156.5 | 93588.2 | 95744.79 |
| 10% Mixed Hydrogen | 100 | 10.0% | 90.0% | 11.52 | 88.02 | 4313.1 | 88662.5 | 92975.63 |
| 15% Mixed Hydrogen | 100 | 15.0% | 85.0% | 17.28 | 83.13 | 6469.6 | 83736.8 | 90206.48 |
| 20% Mixed Hydrogen | 100 | 20.0% | 80.0% | 23.04 | 78.24 | 8626.2 | 78811.2 | 87437.33 |
| 25% Mixed Hydrogen | 100 | 25.0% | 75.0% | 28.8 | 73.35 | 10782.7 | 73885.5 | 84668.18 |
| 30% Mixed Hydrogen | 100 | 30.0% | 70.0% | 34.56 | 68.46 | 12939.3 | 68959.8 | 81899.02 |

In an embodiment, a pre-existing distribution system is adapted to determine a concentration of mixed gas using speed of sound techniques herein. In an embodiment, it is adapted without adding to the existing distribution components of the distribution system any additional distribution component that provides the container/measuring chamber at the measuring point where the speed of sound is measured by the wave sensor(s). That is, one of the existing distribution components provides the container/measuring chamber.

In an embodiment, steps (e.g. a method) to adapt a distribution system comprise:

A. selecting an existing component of the distribution system to define a measuring chamber;

B. adapting the measuring chamber with ultrasound sensors (e.g. a sensor wave generator and a sensor wave detector) to generate and detect a wave signal;

C. if not known, determining a distance of travel of the wave signal; and

D. configuring an ultrasound sensor device or system (e.g. a processing unit) to determine and present at least one of speed of sound of mixed gas and data determined therefrom in response to wave signals from the wave sensors.

Configuring may include configuring the ultrasound sensors such as with data representing the distance travelled.

Steps may include adapting the measuring chamber with a reflective sensor 202. Steps may include adapting the measuring chamber with a temperature sensor coupled to the processing unit to provide a temperature signal with which to determine data determined from the speed (e.g. the gas concentration/ratio, total moles (e.g. for each type of gas or in the aggregate), total BTUs (e.g. for each type of gas or in the aggregate), etc.).

In an embodiment, such as where any of flow rate, pressure, vibration, and temperature are measured, steps may include configuring the processing unit with a measuring chamber threshold for use to provide at least one of an alarm signal and a control signal in response to operation of the distribution system outside the threshold.

In an alternative embodiment, step a. above is replaced with a step of adding a component that defines the measuring chamber having a known volume.

In an embodiment, components 102, 108, 110 comprise an ultrasound sensor device. In an embodiment, components 102, 108, 110 and 202 comprise an ultrasound sensor device.

In an embodiment, an ultrasound sensor device with a controller board (e.g. 120) comprise an ultrasound sensor system.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. An ultrasound sensor device comprising:
a measuring chamber; and
an ultrasound sensor coupled to the measuring chamber to generate ultrasound signals in a flow of mixed gas for transmission perpendicularly to the flow with which to determine a speed of sound in the flow, each respective gas of the mixed gas providing a respective energy value with which to determine a total energy value for the flow of mixed gas;
wherein:
the ultrasound sensor is coupled to provide ultrasound signals or the speed of sound to a processing unit, the processing unit configured to determine a concentration of the respective gases in the mixed gas in response to the speed of sound; and
the processing unit is further configured to present at least one of the speed of sound, the concentration of the respective gases or other data determined from the speed of sound to determine the total energy value of the mixed gas.

2. The ultrasound sensor device of claim 1, further comprising a temperature sensor to measure temperature in the chamber, the temperature sensor providing temperature signals to the processing unit with which to determine data determined from the speed of sound.

3. The ultrasound sensor device of claim 1, wherein the ultrasound sensor comprises a sensor wave generator and sensor wave detector positioned on a same side of the measuring chamber to receive a reflected wave signal from a reflective sensor positioned on an opposite side of the measuring chamber.

4. The ultrasound sensor device of claim 1, wherein the measuring chamber is a pre-existing component of a distribution system adapted with the ultrasound sensor, the distribution system configured to distribute mixed gas to supply energy to any one or more of residential, commercial, or industrial customers.

5. An ultrasound sensor system comprising:
a processing unit;
a measuring chamber for coupling to receive a flow of mixed gas;
an ultrasound sensor coupled to the measuring chamber to generate ultrasound signals in the flow of mixed gas for transmission perpendicularly to the flow with which to determine a speed of sound in the flow, each respective gas of the mixed gas providing a respective energy value with which to determine a total energy value for the flow of mixed gas;
wherein:
the ultrasound sensor is configured to provide ultrasound signals or the speed of sound to the processing unit; and
the processing unit is configured to:
determine a concentration of the respective gases in the mixed gas in response to the speed of sound; and
present at least one of the speed of sound, the concentration of the respective gases or other data determined from the speed of sound to determine the total energy value of the mixed gas.

6. The ultrasound sensor system of claim 5, wherein the processing unit is configured to determine the concentration of the respective gases in accordance with the adiabatic constant of the mixed gas and the mole value of the mixed gas.

7. The ultrasound sensor system of claim 5, wherein the processing unit determines the concentration of the respective gases in accordance with the speed of sound in the mixed gas $V_s$ in accordance with the equation:

$$V_s = \sqrt{\frac{\gamma RT}{M}},$$

where $\gamma$ is the adiabatic constant of the mixed gas, R is the gas constant, T is the temperature and M is the molar mass of the mixed gas.

8. The ultrasound sensor system of claim 7, wherein the mixed gas is a binary gas and wherein $\gamma$ is determined with the equation:

$$\gamma_{mixture} = 1 + \left(\frac{X}{\gamma_1 - 1} + \frac{1-X}{\gamma_2 - 1}\right)^{-1}$$

where X is the molar fraction of a first gas of the mixed gas; and
wherein M is determined with the equation:

$$M_{mixture} = XM_1 + (1-X)M_2$$

where $M_1$ and $M_2$ are the molar mass of the first gas and a second gas of the mixed gas.

9. The ultrasound sensor system of claim 5, wherein a gas type of each respective gas in the mixed gas is known to the processing unit.

10. The ultrasound sensor system claim 5, wherein the processing unit is coupled to an alarm device, the processing unit signalling an alarm in response to a measuring chamber threshold.

11. The ultrasound sensor system of claim 5, wherein the processing unit is coupled to a control system, the processing unit providing a control signal in response to a measuring chamber threshold to control a flow within the measuring chamber.

12. The ultrasound sensor system claim 5, wherein the processing unit is coupled to an off-board device to communicate any one of the speed of sound and data determined from the speed of sound.

13. The ultrasound sensor system of claim 5, wherein the ultrasound sensor comprises a sensor wave generator and sensor wave detector positioned on a same side of the measuring chamber to receive a reflected wave signal from a reflective sensor positioned on an opposite side of the measuring chamber.

14. A meter set comprising:
a meter body for receiving a flow of mixed gas, each respective gas of the mixed gas providing a respective energy value with which to determine a total energy value for the flow of mixed gas; a meter set processing unit; and an ultrasound sensor;
wherein:
   the ultrasound sensor is coupled to the meter body to generate ultrasound signals in the flow of mixed gas for transmission perpendicularly to the flow with which to determine a speed of sound in the flow;
   the ultrasound sensor is configured to provide ultrasound signals or the speed of sound to the meter set processing unit; and
   the meter set processing unit is configured to:
      determine a concentration of the respective gases in the mixed gas in response to the speed of sound; and
      present at least one of the speed of sound, the concentration of the respective gases or other data determined from the speed of sound to determine the total energy value of the mixed gas.

15. The meter set of claim 14 further comprising:
a pressure sensor to measure pressure in the meter set; and
a flow sensor responsive to the flow of gas through the meter set to measure gas volume, flow rate or both.

16. The meter set of claim 14, wherein:
a. the meter body comprises an inlet to receive the flow of mixed gas and an outlet to provide the flow of mixed gas;
b. one of the inlet or the outlet defines a measuring chamber to measure the speed of sound; and
c. the ultrasound sensor comprises a sensor wave generator and sensor wave detector positioned on a same side of the measuring chamber to receive a reflected wave signal from a reflective sensor positioned on an opposite side of the measuring chamber.

17. A method to adapt a distribution system configured to distribute mixed gas to supply energy to any one or more of residential, commercial, or industrial customers, each respective gas of a flow of mixed gas providing a respective energy value with which to determine a total energy value for the flow of mixed gas:
a. selecting an existing component of the distribution system to define a measuring chamber;
b. adapting the measuring chamber with an ultrasound sensor to generate a wave signal in the flow for transmission perpendicularly to the flow;
c. determining a distance traveled of the wave signal generated and detected by the ultrasound sensor; and
d. configuring a processing unit to determine and present at least one of a speed of sound of a mixed gas flowing in the measuring chamber or data determined from the speed of sound to determine the total energy value of the mixed gas at the existing component.

18. The method of claim 17 comprising adapting the measuring chamber with a temperature sensor coupled to the processing unit to provide temperature signals with which to determine the speed of sound.

19. The method of claim 17 comprising configuring the processing unit with a measuring chamber threshold for use to provide at least one of an alarm signal and a control signal in response to operation of the distribution system outside the measuring chamber threshold.

20. The method of claim 17, wherein the ultrasound sensor comprises a sensor wave generator and sensor wave detector positioned on a same side of the measuring chamber to receive the wave signal as reflected from a reflective sensor positioned on an opposite side of the measuring chamber.

* * * * *